United States Patent [19]

Yount

[11] Patent Number: 4,968,137

[45] Date of Patent: Nov. 6, 1990

[54] DEVICES AND PROCEDURES FOR IN VITRO TESTING OF PULSE OXIMETRY MONITORS

[75] Inventor: John E. Yount, Beaverton, Oreg.

[73] Assignee: The State of Oregon Acting by and through the State Board of Higher Education on Behalf of Oregon Health Sciences University, Eugene, Oreg.

[21] Appl. No.: 358,794

[22] Filed: May 30, 1989

Related U.S. Application Data

[63] Continuation-in-part of Ser. No. 938,275, Dec. 5, 1986, Pat. No. 4,834,532.

[51] Int. Cl.$^5$ .............................................. G01N 33/48
[52] U.S. Cl. ........................................ 356/41; 356/42; 356/243; 250/252.1; 128/633
[58] Field of Search ...................... 356/39, 40, 41, 42, 356/243; 250/252.1; 128/632, 633

[56] References Cited

U.S. PATENT DOCUMENTS

| 4,167,331 | 9/1979 | Nielsen. | |
|---|---|---|---|
| 4,650,327 | 3/1987 | Ogi. | |
| 4,744,656 | 5/1988 | Moran et al. | 356/42 X |

FOREIGN PATENT DOCUMENTS

0102816  8/1983  European Pat. Off.
0104771  8/1983  European Pat. Off.

OTHER PUBLICATIONS

Mark Yelderman and William New, "Evaluation of Pulse Oximetry", *The Journal of Anesthesiology*, vol. 59:349-352 (Oct. 1983).
"Smart Oximeter Helps Trim Saturation Speculation", *Anesthesiology Topics*, vol. 3, No. 3 (May-Jun. 1984).
M. Chung, M.D. et al., "Transcutaneous Monitoring of PO$_2$ and PCO$_2$ During One-Lung Anesthesia", *Anesthesiology*, vol. 61, No. 3A, A164 (Sep. 1984 Supplement).
Christopher Glazener, M.D. et al., "Hypoxemia in Children Following General Anesthesia", *anesthesiology*, vol. 61, No. 3A, A164 (Sep. 1984 Supplement).
D. P. Lobo, M.D. et al., "Monitoring High Frequency Jet Ventilation During Anesthesia", *Anesthesiology*, vol. 61, No. 3A, A171 (Sep. 1984 Supplement).
F. G. Mihm, M.D. et al., "Non-Invasive Monitoring of Respiratory Failure with Pulse Oximetry and Capnography", *Anesthesiology*, vol. 59, No. 3, A136 (Sep. 1983 Supplem't).
Frank Monaco, et al., "Continuous Noninvasive Oxygen Saturation Monitoring in Sick Newborns", *Respiratory Care*, vol. 28, No. 10 (Oct. 1983).

(List continued on next page.)

*Primary Examiner*—David Mis
*Attorney, Agent, or Firm*—Klarquist, Sparkman, Campbell, Leigh & Whinston

[57] ABSTRACT

A device and method for calibration of pulse oximeters is disclosed. A standard specimen that has optical characteristics of hemoglobin of a known oxygen saturation is placed in the light path of a pulse oximeter probe. The image of a pulse is created by a filter that periodically increases and decreases the amount of light allowed to reach the sensor of the probe. In one embodiment, the filter comprises a pair of polarizing filters rotated with respect to one another under the control of a digital computer with a motor interface device. In another embodiment, a wedge of a light-attenuating medium, such as a cuvette containing oxygenated blood, is reciprocated in the light path, the wide portions of the wedge attenuating a greater amount of light than the narrow portions. Such a cuvette can include filler openings, with outwardly extending tubes at both the wide and narrow ends. For comparison testing, the cuvette can include a sample of blood from a test subject, the blood having been oxygenated to a known oxygen content. A light-attenuating layer, with light transmissivity characteristics that are additive to those of the filter, can be provided in the light path to simulate an abnormal blood condition, such as the presence of carboxyhemoglobin, methemoglobin, or venous blood.

17 Claims, 3 Drawing Sheets

OTHER PUBLICATIONS

M. S. Shulman, M.D., et al., "Non-Invasive Pulse Oximetry During One-Lung Ventilation", *Anesthesiology*, vol. 61, No. 3A, A98 (Sep. 1984 Supplement).

David B. Swedlow and Sydney Stern, "Continuous Non-Invasive Oxygen Saturation Monitoring in Children with a New Pulse-Oximeter", *Critical Care Medicine*, vol. 12, No. 3 (Mar. 1983).

Andrew R. Wilkerson, et al., "Continuous in Vivo Oxygen Saturation in Newborn Infants with Pulmonary Disease", *Critical Care Medicine*, vol. 7, No. 5 (May 1979).

Andrew R. Wilkerson, et al., "In Vivo Oxygen Dissociation Curves in Transfused and Untransfused Newborns with Cardiopulmonary Disease", *American Review of Respiratory Disease*, 122:629–634 (1980).

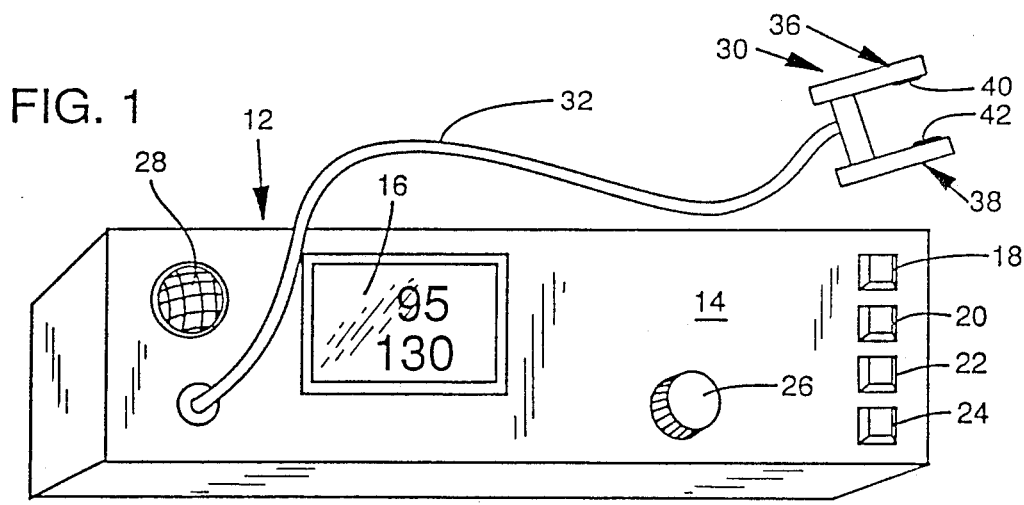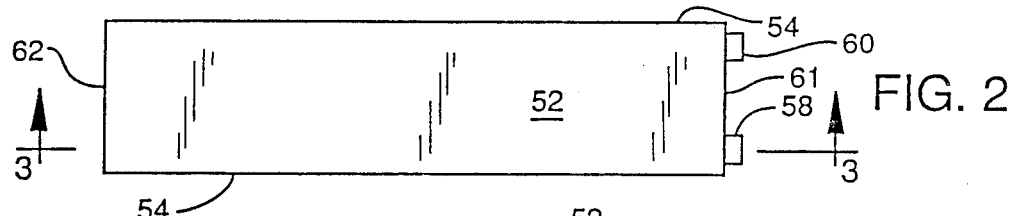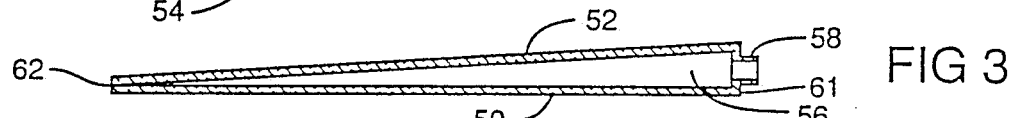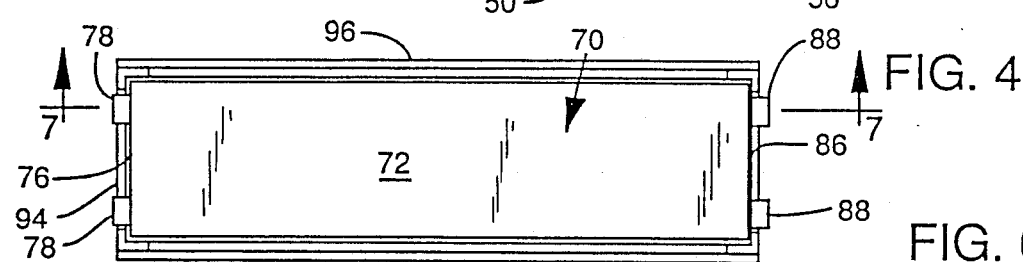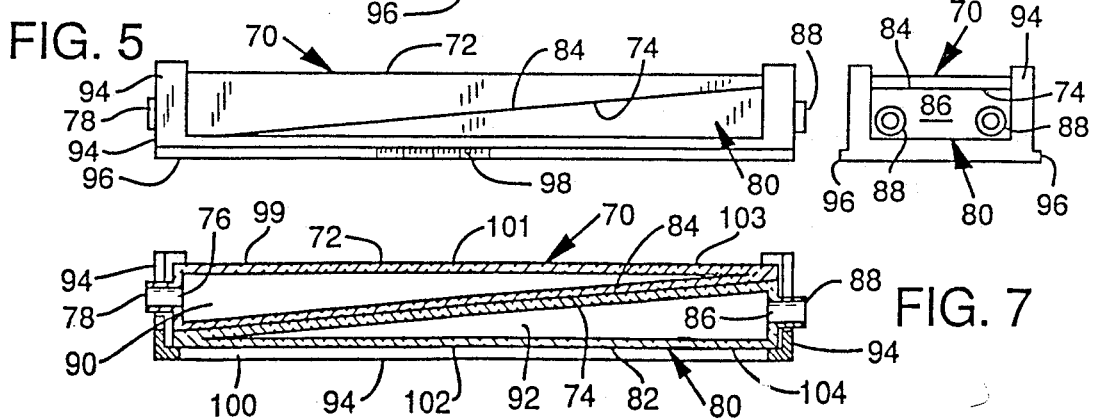

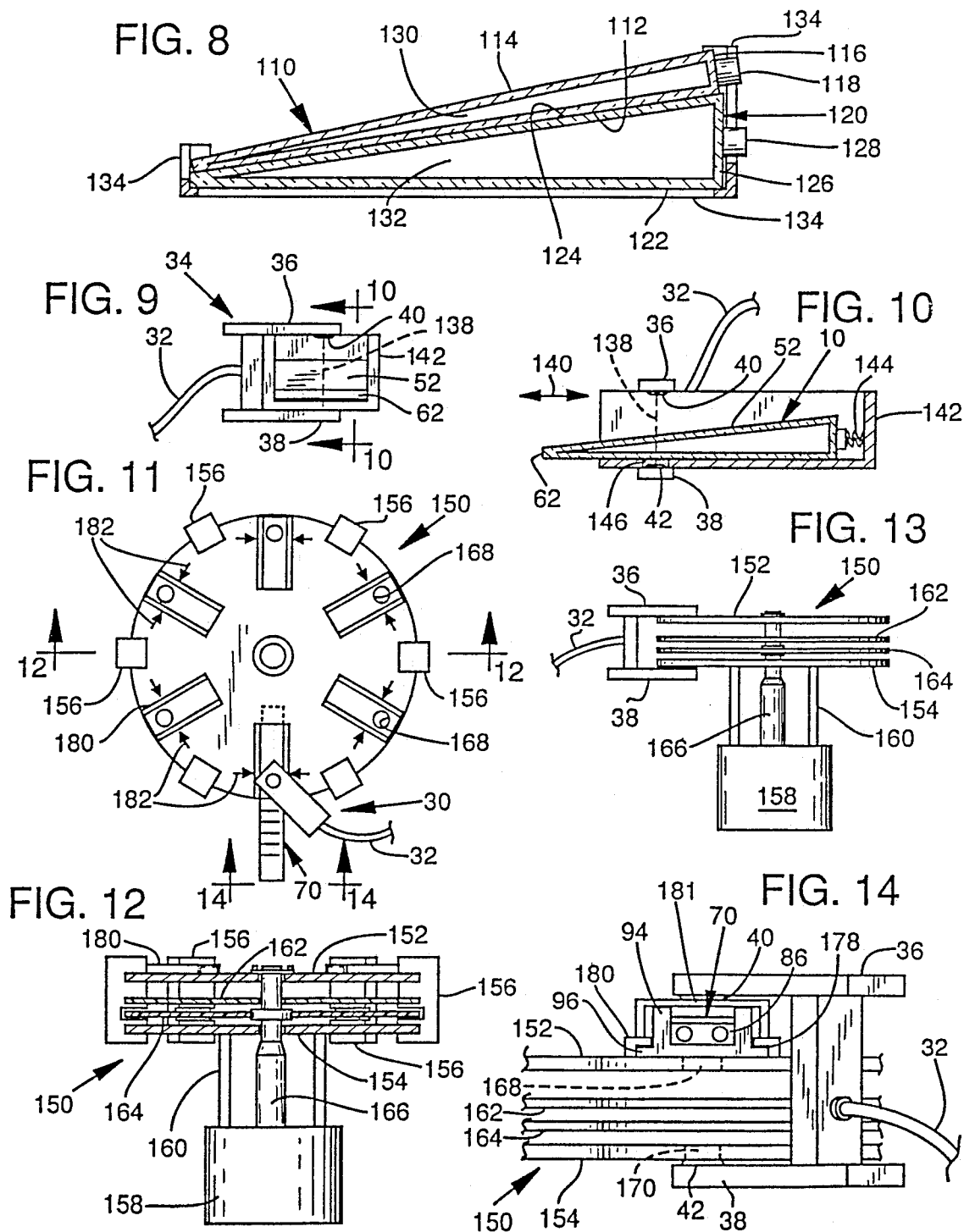

DEVICES AND PROCEDURES FOR IN VITRO TESTING OF PULSE OXIMETRY MONITORS

This is a continuation-in-part of application Ser. No. 06/938,275, filed Dec. 5, 1986, now U.S. Pat. No. 4,834,532, incorporated herein by reference.

BACKGROUND OF THE INVENTION

1. Field of the Invention

This invention concerns pulse oximeters, and more particularly devices and methods for testing or calibrating pulse oximeters.

2. General Discussion of the Background

Continuous assessment of arterial oxygenation is important in the treatment of critically ill or anesthesized patients. Such individuals are often dependent upon artificial life support systems which sufficiently oxygenate their blood to prevent permanent physical impairment, brain damage, or death. Blood oxygen concentration levels in such patients must be carefully maintained within a narrow range to prevent serious physical consequences. Premature infants, for example, must have a blood oxygen content below about 95% to prevent retinal damage and above about 90% to prevent respiratory distress.

Several methods have been devised for continuously monitoring blood oxygen levels. Many of these methods involve invasive removal of blood for analysis, which provides only intermittent information. Transcutaneous oxygen tension measurement provides continuous information but requires special site preparation, airtight probe mantling and a potentially harmful local heat source to induce arterialization. In addition to these serious drawbacks, transcutaneous oxygen monitoring often fails accurately to reflect true arterial oxygenation.

Pulse oximeters, such as those shown in U.S. Pat. No. 4,167,331, European patent application Publication No. 0 104 771, and European patent application Publication No. 0 102 816 are most convenient for monitoring blood oxygen concentrations. Such pulse oximeters function by positioning a pulsating arterial vascular bed between a two wavelength light source and a detector. The pulsating vascular bed, by expanding and relaxing, creates a change in the light path length that modifies the length detected and results in a plethysmograph waveform. The amplitude of the varying detected light depends on the size of the arterial pulse change, the wavelength of light used, and the oxygen saturation of the arterial hemoglobin. The detected pulsatile waveform is produced solely from arterial blood using the amplitude of each wavelength and Beer's law. An exact beat-to-beat continuous calculation of arterial hemoglobin oxygen saturation can thereby be obtained with no interference from surrounding venuous blood, skin, connective tissue, or bone.

A typical pulse oximeter includes a probe which is attached on either side of a distal digit, such as the tip of a finger. The probe includes the light source and the detector which are held in opposing relationship to one another on either side of the finger such that the light source directs a beam of light through the finger and towards the detector. Most pulse oximeters use simple detecting circuitry with diodes that have broad spectral sensitivity. The light source emits wavelengths of red and infrared light which correspond to absorption peaks of oxyhemoglobin and deoxyhemoglobin in red blood cells entering the capillaries during systoly. A background absorption occurs from the hemoglobin remaining in small vessels during diastoly and from general tissue absorption. By rapidly alternating the wavelengths of light transmitted through the tissue, the difference in absorption for total hemoglobin and oxyhemoglobin can be measured for each pulse of arterial capillary blood. An estimated percentage of oxygenated hemoglobin in each pulse can then be calculated from the difference in absorption.

Several pulse oximeters employing these principles are now available. The Nellcor pulse oximeter Model N-100 is available from Nellcor Inc. of Hayward, Calif. Other such devices include the Ohmeda Biox 3700 pulse oximeter and the Novametrix pulse oximeter.

Although pulse oximeters are valuable tools in continuously monitoring oxygenation levels of blood hemoglobin, there is presently no way for a user to test whether a pulse oximeter is accurate. A rotating blade of a graded neutral density filter material is proposed as a calibration device in European patent application Publication No. 0 102 816. But, making such a graded neutral density filter would require a major engineering effort. No such filter material is now known to exist. A careful and convenient method of calibrating pulse oximeters is needed since the oxygenation level of a patient's blood hemoglobin must be maintained within a narrow and often critical range. Slight deviations from the range must be accurately detected by the oximeter.

It is therefore an object of the present invention to provide a device and method for testing and calibrating pulse oximeters.

It is yet another object of the invention to provide such a device which is convenient and simple to use.

The foregoing and other objects and advantages of the invention will become more apparent from the following detailed description of the preferred embodiments which proceed with reference to the accompanying drawings.

SUMMARY OF THE INVENTION

The foregoing objects are achieved by providing the detector probe of a pulse oximeter with an artificial image of a pulse by periodically varying the intensity of light received by the light detector of the probe. This is accomplished by placing, in the light path of the probe, a unique filter system having a light transmissivity which can be gradually and periodically varied to simulate a desired pulse rate. A sample of material which simulates hemoglobin of a known oxygen content is also placed in the light path between the source and detector. The readouts for the pulse rate and oxygenated hemoglobin content can then be compared with the known reciprocation rate and oxygen concentration. If the pulse oximeter has detected values different from the induced pulse and known oxygen content of the standard sample, the oximeter can be replaced or adjusted to match the known values. Or this measured degree of error can be taken into consideration when interpreting readings from the oximeter.

In one embodiment of the calibrating device, the pulse is simulated by means of a light-absorbing, wedge-shaped member located between the light source and the light detector. The member is longitudinally reciprocated at a known rate along a path generally perpendicular to the light path. The progressively increasing thickness of the wedge as it moves in one direction reduces the amount of light transmitted through the wedge to the detector, while the progressively decreasing thickness of the wedge as it moves in the opposite direction increases the amount of light detected. Reciprocal movement of the wedge therefore creates, for the detector, the image of a pulse at a known rate. The wedge member can be a vessel which contains hemoglobin having a known oxygen content. The known values for pulse rate and oxygen percentage are compared with the detected values computed by the oximeter. The special blood conditions of a patient can be simulated by using a sample which simulates the transmivity of the patient's blood. The patient's own blood, oxygenated to a known oxygen content, can be used in a wedge-shaped cuvette. Or, multiple samples can be superposed to adjust the transmissivity.

In another embodiment, the pulse images are created by a pair of parallel polarization filters. The detector probe is positioned in relation to the polarization filters such that the light source directs a beam of light through both filters towards the detector. One of the filters is then rotated with respect to the other to sequentially increase and decrease the amount of light received by the detector. A stepping motor can be used to rotate the rotatable filter at a programmed rate to mimic changes in transmittance during a normal physiological pulse. A sample of material which contains or simulates hemoglobin with a known oxygen content is placed in the beam of light which passes between the light source and detector of the probe.

Either embodiment can employ a motor to move the light attenuating element, in response to a timing program. A digital computer can be easily programmed to control such a motor so as to simulate a variety of conditions.

BRIEF DESCRIPTION OF THE DRAWINGS

FIG. 1 is an isometric view of a pulse oximeter.

FIG. 2 is a top plan view of a cuvette for testing the accuracy of a pulse oximeter.

FIG. 3 is a cross-sectional view taken along line 3—3 of FIG. 2.

FIG. 4 is a top plan view of an assembly including a frame and two cuvettes, similar to the cuvette shown in FIGS. 1 and 2, the cuvettes being superposed and tapering in opposite directions.

FIG. 5 is a side elevation of the assembly shown in FIG. 4.

FIG. 6 is a front elevation of the assembly shown in FIG. 4.

FIG. 7 is a cross-sectional view taken along line 7—7 of FIG. 4.

FIG. 8 is a cross-sectional view of two superposed cuvettes of different tapers, the cuvettes tapering in the same direction.

FIG. 9 is a front elevational view of a detector probe of a pulse oximeter being tested by reciprocating movement of a cuvette of the type shown in FIGS. 2 and 3.

FIG. 10 is a cross-sectional view taken along line 10—10 of FIG. 9.

FIG. 11 is a top plan view of an optical bench device for testing the accuracy of a pulse oximeter.

FIG. 12 is a cross-sectional view taken along line 12—12 of FIG. 11.

FIGS. 13 and 14 are schematic views of a detector probe of a pulse oximeter connected to the optical bench testing device of FIGS. 11 and 12.

DETAILED DESCRIPTION

Figure 15:
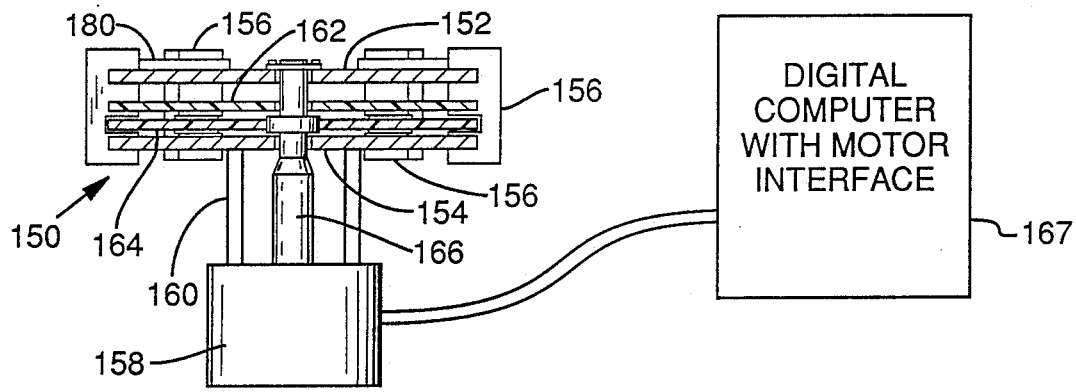
FIG. 15 is a schematic view showing the probe and testing device of FIG. 13, the testing device being under the control of a digital computer.

FIGS. 2-14 show several embodiments of devices for testing the accuracy of a pulse oximeter, such as those oximeters shown and described in U.S. Pat. No. 4,167,331 and European patent application Publication Nos. 0 102 816 and 0 104 771, all of which are incorporated herein by reference. Commercial embodiments of the pulse oximeter with which the calibration device can be used include the Nellcor pulse oximeter Model N-100, the Ohmeda Biox 3700, and the Novametrix pulse oximeter.

FIG. 1 illustrates a pulse oximeter 12 which includes a box-like housing 14, display screen 16, push button controls 18, 20, 22, 24, control knob 26, and speaker 28 through which acoustic signals and alarms are sounded. Oximeter 12 gathers data through a detector probe 30 which is connected to oximeter 12 through lead line 32. Detector probe 30 includes jaw members 36, 38 which are spring biased toward each other and suitably dimensioned to fit snugly around the tip of a human finger or earlobe with top member 36 resting, for example, on the flat surface of a human fingernail while bottom member 38 is secured on the opposing side of the fingertip. Top member 36 carries a light emitting diode 40 while bottom member 38 carries a light sensor 42. A more detailed discussion of the structure and operation of the pulse oximeter is not given here since it is more fully explained in the above-cited patents and published patent applications.

The present invention involves a method and apparatus for simulating the periodic light transmissivity shifts which result from the pulsing of blood through an arterial vascular bed and a standard sample of a material which has the optical characteristics of hemoglobin of a known oxygen content.

Oxygen Content Standard

A most convenient and flexible way of creating a hemoglobin oxygenation standard is to use a vessel containing blood of a known oxygen content.

FIGS. 2 and 3 show such a vessel in the form of a cuvette or wedge 10 which has a flat bottom 50 and a slanted top 52 interconnected by a sidewall 54. Wedge 10 is preferably made of an optical quality quartz glass or similar material of a known optical density and defines a chamber 56. Access to the chamber is provided by a pair of capillary filling tubes 58, 60 through sidewall 54 at the base end 61 of wedge 10.

The chamber 56 flares from a minimal thickness at a narrow end 62 at the region of wall intersection of wedge 10 to a thickness of one millimeter at the base end 61 where capillary tubes 58, 60 enter wedge 10. In other embodiments of the wedge, the height of chamber 56 can be different, for example, two millimeters, three millimeters, four millimeters, and so on at the base end 61. The thickness of each glass surface, such as surfaces 50, 52, 54 is one millimeter.

Each wedge 10 is filled with a material which has the optical characteristics of blood of a known oxygen content. In the illustrated embodiment, this material is microbiological media, consisting of 5% sheep's blood in agar, that has been equilibrated with a known gas mixture before being introduced into wedge 10 through capillary tubes 58, 60. Once the media is introduced into chamber 56, tubes 58, 60 are sealed either by a cap or heat sealing to provide an airtight sample. Wedge 10 can then be stored in a refrigerator until use.

Although 5% sheep's blood is used as the known sample in this embodiment, human blood suspended in a matrix such as agar and having hemoglobin of a known oxygen concentration can also be used. It is preferable to use a sample having about 5% blood suspended in the matrix since about 5% to 8% of finger tissue is comprised of blood. Agar is a preferred matrix material because it reasonably simulates tissue and can easily be flushed from the chamber 56 so that the wedge can be reused. When blood is used in the medium, the samples are best prepared just shortly before the time of calibration. Otherwise, steps should be taken to stabilize the blood. For more stable samples, blood of a known oxygen content can be frozen. Also, deglycerolized blood cells can be used.

Wedges, such as wedge 10, can be combined with other wedges of the same thickness or other thicknesses for their additive effect. FIGS. 4–7, for example, show a top wedge 70 having a flat face 72, slanted face 74, upright end wall 76, and capillary filling tubes 78. A bottom wedge 80 similarly includes a flat face 82, slanted face 84, upright wall 86, and filling tubes 88. Wedges 70 and 80 are both filled with media which contains 5% calf's blood. Medium 90 of wedge 70 contains hemoglobin which is completely unsaturated with oxygen, while medium 92 of wedge 80 contains hemoglobin which is 100% saturated. Wedge 70 is placed on top of wedge 80 with slanted faces 74, 84 abutting such that wedges 70, 80 cooperatively form a rectangular box with tubes 78, 88 extending from opposite ends of the box. The wedges 70, 80 are held in precise alignment by inserting them snugly in a rigid frame 94. The frame includes ribs 96. Graduation indicia 98 are provided on the frame 94 for precise alignment of the frame with other equipment.

When wedges 70, 80 are arranged as shown in FIGS. 4–7, they form a calibrating device which has a progressively changing concentration of oxygenated hemoglobin along the length of the box. For example, a light beam which shines through the box from a location 99 and is detected at a location 100, will shine through completely deoxygenated hemoglobin, while light that shines through the box from location 101 can be detected at location 102 as being 50% oxygenated. Light that shines through the box from location 103 will be detected at location 104 as shining through hemoglobin which is 100% saturated with oxygen.

Yet another arrangement of wedges is shown in FIG. 8. A top wedge 110 includes a flat face 112, slanted face 114, a one millimeter high upright end wall 116, and capillary filling tube 118. Bottom wedge 120 similarly includes a flat face 122, slanted face 124, a four millimeter high upright end wall 126, and filling tube 128. Top wedge 110 is filled with a biologic medium 130 which contains hemoglobin which is completely unsaturated with oxygen. Wedge 120, however, is filled with a biologic medium 132 which contains 100% oxygen saturated hemoglobin. The wedges are placed in a frame 134 with wedge 110 on top of wedge 120 with bottom face 112 of wedge 110 abutting slanted face 124 of wedge 120 such that tubes 118, 128 are aligned, one above the other.

The combined wedge which results from the combination of wedges 110, 120 as shown in FIG. 8 will appear to probe detector 30 to have hemoglobin with an 80% concentration of oxygen along its entire length. Wedges of varying heights can be similarly juxtaposed to provide a multilayered calibrating wedge which appears, when scanned by a pulse oximeter probe, to have any desired hemoglobin oxygen content. The following chart illustrates some combinations of wedges which can be used to calibrate pulse oximeters at differing oxygen concentrations.

| Oxygen Concentration Detected | 100% | 80% | 60% | 40% | 20% |
|---|---|---|---|---|---|
| Height of 100% Concentration Wedge | 4 mm | 4 mm | 3 mm | 2 mm | 1 mm |
| Height of 0% Concentration Wedge | 0 mm | 1 mm | 2 mm | 3 mm | 4 mm |

Other simulations can be accomplished using multiple layers of cuvettes. In particular, if a subject is known to have blood of unusual characteristics, a comparative test assembly can include a cuvette with a sample to adjust the transmissivity so that the assembly simulates the unusual blood condition. Examples of such conditions include the presence of methemoglobin, carboxyhemoglobin (found in the blood of smokers), and sulfhemoglobin. Using two cuvettes, it is also possible to simulate the higher than normal proportion of venuous blood found in newborns. Calibratible oximeters can be adjusted using such samples which simulate the subject's particular blood condition. For nonadjustable oximeters, data can be obtained on whether the readout is shifted due to a nonstandard blood composition.

Calibration can also be accomplished by taking a sample of the blood of the patient who is to use the oximeter (or the blood of a subject with a similar blood condition). The blood is oxygenated to a desired oxygen content, then the oxygenated sample is used in a single cuvette. The tested oximeter is then adjusted (if possible) to display the previously known oxygen content of the test sample. Testing with a patient's own blood would take into account any unknown pecularities of the patient's blood. Oxygenated blood can be prepared by a local blood bank to serve as the reference sample.

Wedges of an artificial light transmissive material could also be used so long as they have the optical characteristics of hemoglobin at the light frequencies employed by the probe.

Moving Cuvette Pulse Generator

In a first embodiment of the invention, a simulated pulse signal is provided by reciprocating a wedge 10, filled with blood of a known oxygen content, (or an assembly of the type shown in FIG. 8) between diode 40 and sensor 42, in a plane generally perpendicular to the light path as shown in FIG. 9.

Wedge 10 is first filled with a medium such as 90 or 92 having hemoglobin of a known oxygen concentration. The wedge 10 is then inserted between members 36, 38 such that a beam 138 of light emitted by LED 40 passes through surfaces 52 and 50. For convenience the wedge 10 may be contained in a channel member 142 that has a compression spring 144 positioned to engage the end wall 61 of the wedge. The probe 30 can be clipped to the channel member 142 such that the jaw 36 engages an upper edge of the member and the jaw 38 engages the bottom of the member with the sensor 42 positioned in alignment with an opening 146 through the bottom of the member. Wedge 10 is then periodically moved, by hand pushing the narrow end 62 or by machine, along an axis of movement indicated by directional arrow 140.

As wedge 10 is progressively moved (to the left in FIG. 9) through jaw 34, the intensity of light from the LED 40 which is transmitted through the wedge 10 and detected at sensor 42 grows progressively less as progressively thicker portions of wedge 10 pass between the LED 40 and the sensor 42. The resulting reduction in transmissivity of light through the wedge mimics the reduction in transmissivity that occurs in human tissues as blood surges through the tissues, engorges it with blood, and expands the capillary bed and surrounding tissue. When wedge 10 is handheld, the operator moves it through jaw 34 at a known rate that imitates a normal human pulse. To ease operation, the length of the spring 144 can be selected so that, as the spring travels between fully extended and fully compressed positions, the wedge 10 is moved an appropriate distance to simulate the degree of transmissivity shift observed in living subjects. For even greater precision, the wedge can be reciprocated by a machine at a preselected reciprocation rate and distance. Since the reciprocation rate is known, it can be compared to the pulse rate displayed on screen 16 of oximeter 12. The oxygen saturation of hemoglobin within wedge 10 is also known, and it can similarly be compared to the oxygen concentration level shown on screen 16.

Alternatively, the wedge can be rotated along a curved path, rather than be moved in a straight line. In such a rotating wedge embodiment, the wedge can be continuously rotated, rather than reciprocated, if the wedge is constructed to start from a narrow edge, widen to a central region, then taper back to a second narrow edge. As such a wedge rotates, the sample progressively thickens, then progressively thins in the light path.

Polarizing Filter Pulse Generator

Another embodiment of the calibrating device, shown in FIGS. 11–14, employs an optical bench which uses a pair of polarizing discs to simulate the changing light transmissivities that imitate a human pulse. The optical bench 150 includes a top, round steel plate 152, and bottom round steel plate 154 which are held in parallel, spaced relationship to each other by a plurality of plastic brackets 156. Bottom plate 154 is held above a stepping motor 158 by four steel struts 160. The stepping motor can be, for example, a Slo-Syn synchronous stepping motor manufactured by Superior Electric Company of Bristol, Conn.

Sandwiched between plates 152, 154 are polarizing discs 162, 164. Top disc 162 is mounted stationary below plate 152, while lower plate 164 is attached to and rotatably driven by drive shaft 166 of motor 158. The stepping motor 158 can be controlled by a standard timing mechanism, or as in FIG. 15, by a digital computer 167 with a suitable interface device for controlling the motor 158. The computer 167 or timing mechanism is programmed to rotate the lower plate as described below.

Plate 152 is provided with a plurality of openings 168 along the peripheral edge of plate 152. Each of these openings is aligned with an identical opening 170 through bottom plate 154.

In the optical bench embodiment, a wedge or plurality of juxtaposed wedges can be used as the sample of hemoglobin material. For example, a pair of wedges 70, 80, juxtaposed as shown in FIGS. 4–7, can be positioned over an opening 168 as shown in FIGS. 11 and 14. FIG. 14 shows a detailed view wherein the ribs 96 of the frame 94 are slidably received in alignment channels 178 of a track 180 adjacent the opening 168. As shown in FIG. 14, a transparent plastic or glass cover 181 may be present over the track 180 so that the position of the wedge assembly can be adjusted after the probe is attached. The tracks 180 can be mounted in a fixed position on the plate 152 or can be attached by a gear drive mechanism (not shown) of the type used to position slides on a microscope table. Such a gear drive mechanism would allow very precise adjustment of the position of the wedge assembly. Each pair of wedges is calibrated to indicate the known oxygen concentration or other known characteristic of the sample at various points along the pair of wedges. Indicia 98 on the frame 94 can be aligned with indicia 182 on the plate 152 to indicate that when a particular portion of the wedge assembly is aligned between openings 168, 170. By positioning the wedge assembly at different locations, different known oxygen concentrations or other known blood characteristics can be presented in the light path from the LED 40 to the sensor 42.

In operation, as shown in FIGS. 13 and 14, jaw members 36, 38 of detector probe 30 are secured to the optical bench by placing top member 36 on top of plate 152 with LED 40 shining through one of openings 168. Bottom member 38 is correspondingly positioned against bottom plate 154 with light sensor 42 being exposed through an opening 170 immediately below one of the openings 168.

The assembly wedges 70, 80 in frame 94 is then moved to a position in alignment with the pair of opposing holes 168, 170 such that hemoglobin of a known oxygen saturation will be detected by light shining through the pair of opposing holes 168, 170 and the wedge assembly. Stepping motor 158 is next actuated to reciprocatingly rotate polarizing disc 164 relative to stationary polarizing disc 162 at a programmed rate. As disc 164 rotates, the amount of light transmitted from the LED 40 to the sensor 42 varies at a rate that mimics the variation of light transmissivity through a finger during normal human pulsation. The angular velocity of rotating disc 164 can be preselected to be of a known value such that the pulse reading of oximeter 12 can be compared to the preselected known value of the pulse and the accuracy of the oximeter's pulse reading thereby determined. Similarly, the known oxygen saturation of hemoglobin encountered by a beam of light as it passes from LED 40 to sensor 42 can be compared to the concentration percentage that appears on screen 16 of oximeter 12.

In the illustrated embodiment, eight openings 168 are provided through plate 152, while eight corresponding openings 170 are provided through bottom plate 154. Up to eight pulse oximeters can be therefore be calibrated simultaneously by attaching the probe sensors of each of the eight oximeters to one of the pairs of corresponding openings through optical bench 150.

Cuvette

Figure 16:
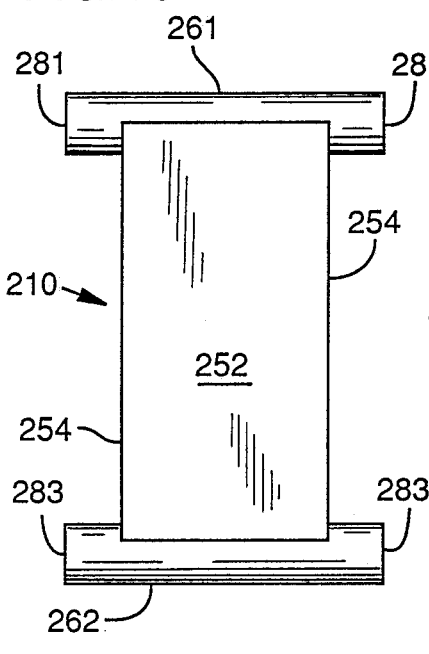
FIG. 16 is a top plan view of another cuvette for testing the accuracy of a pulse oximeter.
Figure 17:
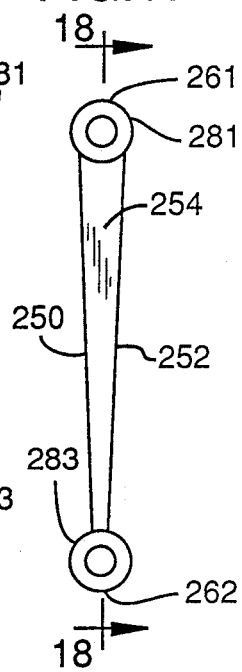
FIG. 17 is a side elevation of the cuvette shown in FIG. 16.
Figure 18:
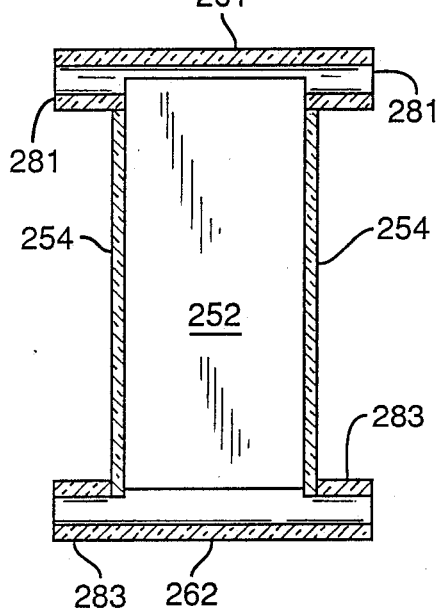
FIG. 18 is a cross-sectional view taken along line 18—18 of FIG. 17.

FIGS. 16–18 show a cuvette 210 design for easy filling and cleaning. The cuvette 210 is similar to the cuvette 10 of FIGS. 2-3, similar features being designated by the same reference numerals incremented by "200." The cuvette 210 differs in that tubes 281 extend from positions adjacent the end wall 261 at the base end. And, tubes 283 extend from positions adjacent the narrow end 262 at the region of wall intersection. The end wall 261 and narrow end 262 in the illustrated cuvette comprise extensions of walls of the tubes 281, 283, respectively. Because tubes 281, 283 provide openings at both ends of the cuvette 210, liquid can be injected and flushed out easily, even at the narrow end 262 of the cuvette 210. Best results are achieved when liquid is injected through one or both tubes 283 at the narrow end 262 and removed through one or both tubes 281 at the base end 261.

Having illustrated and described the principles of the invention in preferred embodiments, it should be apparent to those skilled in the art that the invention can be modified in arrangement and detail without departing from such principles. For example, in the moving cuvette embodiment, a servo motor or other mechanical device could be used to oscillate the cuvette assembly in response to a timing program such as that in the digital computer shown in FIG. 15. Accordingly, I claim all modifications coming within the spirit and scope of the following claims.

I claim:

1. A partially light-transmissive assembly suitable for use as a standard sample to establish the accuracy of a pulse oximeter having an detector probe, the assembly comprising:
   a first body comprising a first sample material, which material simulates the light transmissivity of hemoglobin of a known oxygen saturation;
   a second body comprising a second sample material, the second body being aligned with the first body so that both bodies can be located in the light path of an oximeter detector probe during testing, the second sample material having light transmissivity characteristics that are additive to those of the first sample material such that the combined samples simulate the light transmissivity characteristics of an abnormal blood composition; and
   interconnection means for holding the two samples in a fixed alignment relative to each other.

2. The assembly of claim 1 wherein the second sample material has a transmissivity such that the combined samples simulate the transmissivity characteristics of a subject whose blood contains carboxyhemoglobin.

3. The assembly of claim 1 wherein the second sample material has a transmissivity such that the combined samples simulate the transmissivity characteristics of a subject whose blood contains methemoglobin.

4. The assembly of claim 1 wherein the second sample material has a transmissivity such that the combined samples simulate the transmissivity characteristics of a subject whose blood contains sulfhemoglobin.

5. The assembly of claim 1 wherein the second sample material has a transmissivity such that the combined samples simulate the transmissivity characteristics of a subject who has a higher than normal concentration of venous blood.

6. A method for testing the accuracy of a pulse oximeter which has a light source and a light detector in opposing relationship to one another such that a beam of light travels in a light path that extends from the light source to the detector, the method comprising:
   oxygenating hemoglobin to produce a hemoglobin sample of a known oxygen content;
   placing the sample in the light path of a pulse oximeter to be tested;
   actuating the light source to shine light toward the detector; and
   varying the intensity of light received by the light detector to create the rhythmic image of a pulse.

7. The method of claim 6 wherein the varying comprises moving a polarization filter to periodically increase and decrease the amount of light which passes from the source to the detector.

8. The method of claim 6 wherein the varying comprises moving a body of a light-absorbing medium, along a path between the source and the detector, the body varying in thickness to be progressively changing in light transmissivity along the path.

9. A device for testing the accuracy of a pulse oximeter which comprises a light source and a light detector in opposing relationship to one another such that said source directs a beam of light toward the detector, the device comprising:
   a sample of material which simulates hemoglobin of a known oxygen saturation, the sample being positionable between the source and the detector;
   light intensity potentiometer means for varying the intensity of light received by the detector; and
   digital computer means programmed to control the light intensity potentiometer means so as to create an image of a pulse.

10. The device of claim 9 wherein:
    the potentiometer means is a polarization filter which periodically increases and decreases the amount of light which passes from the source to the detector and a drive mechanism to move the filter; and
    the computer includes an interface device to control the drive mechanism.

11. The device of claim 9 wherein:
    the poteniometer means comprises a body of a light-absorbing medium, which body is moved along a path of movement between the light source and the light detector, and which body varies in thickness to be progressively changing in light transmissivity along the path of movement and a drive mechanism to move the body; and
    the computer includes an interface device to control the drive mechanism.

12. A cuvette for use in testing the accuracy of a pulse oximeter, the cuvette comprising:
    top and bottom walls which are joined at a region of intersection and which diverge from the region at a small acute angle;
    an end wall that is joined to both the top and bottom walls at a distance away from the region of intersection; and
    two spaced apart side walls, each of which is joined to the top, bottom and end walls in such a manner that the cuvette defines a liquid-tight, wedge-shaped chamber;
    at least one of the walls defining a sealable opening through which liquid can be passed to fill or drain the chamber.

13. The cuvette of claim 12 wherein the walls define at least two sealable openings, one of the openings being located adjacent the end wall and the other opening being located adjacent the region of intersection.

14. The cuvette of claim 12 wherein at least two sealable openings are defined adjacent the end wall.

15. The cuvette of claim 12 wherein:

two tubes extend from positions adjacent the end wall to provide two such sealable openings; and two tubes extend from positions adjacent the region of intersection to provide two such sealable openings.

16. The cuvette of claim 12 further comprising, in the chamber, a body of a sample material which simulates venous blood.

17. The cuvette of claim 12 further comprising, in the chamber, a sample of blood of a known oxygen concentration, the blood having been taken from a subject with whom the oximeter is used.

* * * * *